United States Patent [19]

Blankenburg et al.

[11] Patent Number: 5,635,169
[45] Date of Patent: Jun. 3, 1997

[54] SOLUBLE COPOLYMERS FOR HAIR COSMETICS

[75] Inventors: Rainer Blankenburg, Ludwigshafen; Axel Sanner, Frankenthal, both of Germany

[73] Assignee: BASF Aktiengesellschaft, Ludwigshafen, Germany

[21] Appl. No.: 548,726

[22] Filed: Oct. 26, 1995

[30] Foreign Application Priority Data

Oct. 29, 1994 [DE] Germany .................. 44 38 706.7

[51] Int. Cl.⁶ .................................................. A61K 7/06
[52] U.S. Cl. .................................. 424/70.15; 424/70.16; 526/264; 526/263; 526/258
[58] Field of Search ........................ 526/264, 263, 526/258; 424/70.15, 70.16

[56] References Cited

U.S. PATENT DOCUMENTS

| | | | |
|---|---|---|---|
| 4,551,512 | 11/1985 | Straub et al. | 526/264 |
| 4,748,989 | 6/1988 | Nuber et al. | 132/424 |
| 4,767,613 | 8/1988 | Nuber et al. | 424/47 |
| 5,139,770 | 8/1992 | Shih et al. | 424/59 |
| 5,321,110 | 6/1994 | Shih | 526/264 |
| 5,393,825 | 2/1995 | Tseng et al. | 524/548 |

FOREIGN PATENT DOCUMENTS

| | | |
|---|---|---|
| 2040963 | 4/1991 | Canada . |
| 2814287 | 4/1978 | Germany . |

*Primary Examiner*—Margaret W. Glass
*Attorney, Agent, or Firm*—Keil & Weinkauf

[57] ABSTRACT

Copolymers which have K values of from 30 to 50 are obtainable by free radical solution polymerization of A) from 15 to 84.99% by weight of at least one monomer selected from the group consisting of N-vinylpyrrolidone, N-vinylcaprolactam and N-vinylimidazole, B) from 15 to 84.99% by weight of further monoolefinically unsaturated monomers capable of free radical copolymerization and C) from 0.01 to 2% by weight of at least one monomer capable of free radical copolymerization and having at least two non-conjugated olefinic double bonds in alcoholic solution.

6 Claims, No Drawings

SOLUBLE COPOLYMERS FOR HAIR COSMETICS

The present invention relates to copolymers which have K values of from 30 to 50, obtainable by free radical solution polymerization of A) from 15 to 84.99% by weight of at least one monomer selected from the group consisting of N-vinylpyrrolidone, N-vinylcaprolactam and N-vinylimidazole, B) from 15 to 84.99% by weight of further monoolefinically unsaturated monomers capable of free radical copolymerization and C) from 0.01 to 2% by weight of at least one monomer capable of free radical copolymerization and having at least two non-conjugated olefinic double bonds in alcohols.

The present invention furthermore relates to the preparation of such copolymers and to their use in hair cosmetics.

Polymers which are suitable as film formers for hair cosmetics, based on N-vinyl compounds and acrylates and prepared by free radical solution polymerization in alcohols, are disclosed, for example, in German Laid-Open Application DOS 3,627,969, DE-A-33 12 668, DE-A-36 27 970 or DE-A-4 013 872.

DE-A-28 14 287 discloses N-vinylimidazole copolymers which may contain less than 5 mol % of comonomers having two or more copolymerizable double bonds, such comonomers leading to three-dimensionally crosslinked polymers. These copolymers are prepared in water, water/methanol mixtures or organic solvents, such as toluene. The copolymers are suitable as discoloration-inhibiting additives in detergents.

Polymers which are suitable as film formers in hair cosmetics and are based on N-vinyl compounds and acrylates are usually prepared by free radical solution polymerization in alcoholic solutions, the solvents used being in particular the solvents conventionally employed in cosmetics, such as ethanol and/or isopropanol, if necessary as a mixture with water.

Owing to the molecular weight-regulating properties of these alcohols, the specific preparation of polymers having relatively high K values, for example 35-45, may present difficulties. Relatively high K values can be achieved by known processes only at relatively low solvent concentration, which may give rise to problems with heat removal, especially on the production scale.

On the other hand, such relatively high molecular weight polymers have better setting properties on the hair.

It is an object of the present invention to provide relatively high molecular weight film-forming polymers which are suitable for hair cosmetics, can be obtained simply by free radical solution polymerization in alcohols usually used for cosmetics and are readily soluble in these alcohols.

We have found that this object is achieved by the copolymers defined at the outset and a process for their preparation, their use and hair cosmetic compositions containing these copolymers.

According to the invention, suitable monomers A) are heterocyclic N-vinyl compounds selected from the group consisting of N-vinylpyrrolidone, N-vinylcaprolactam and N-vinylimidazole and mixtures thereof. Preferred monomers A) are N-vinylpyrrolidone and N-vinylcaprolactam.

The monomers A) are used in amounts of from 15 to 84.99, preferably from 20 to 80, % by weight.

According to the invention, suitable monomers B) are further monoolefinically unsaturated compounds capable of free radical copolymerization, or mixtures thereof, for example vinyl esters of saturated $C_2$–$C_{24}$-monocarboxylic acids, such as vinyl acetate or vinyl propionate, or vinyl esters of relatively long-chain fatty acids, for example of dodecanoic acid or stearic acid, or vinyl esters of branched fatty acids, such as pivalic acid or versatic acid.

$C_1$–$C_{10}$-Alkyl esters of acrylic acid or of methacrylic acid, for example ethyl acrylate, isobutyl acrylate, N-butyl acrylate, tert-butyl acrylate, methyl methacrylate, ethyl methacrylate, isobutyl methacrylate or N-butyl methacrylate, or the corresponding esters of aminoalkanols, for example N,N-dimethylaminoethyl methacrylate, are also suitable.

Other suitable monomers B) are monomers containing a sulfonate group, such as the salts of 3-acrylamido-2-methylpropanesulfonic acid or 2-acrylamido-2-methylpropanesulfonic acid or preferably the corresponding sodium salts.

Preferred monomers B) are vinyl acetate and tert-butyl acrylate.

According to the invention, the monomers B) were used in amounts of from 15 to 84.99, preferably from 20 to 80, % by weight.

Suitable monomers C) are monomers which are capable of free radical copolymerization and contain at least two nonconjugated olefinic double bonds in the molecule. Examples of suitable monomers are acrylates or methacrylates of saturated polyhydric alcohols, for example 1,4-butanediol diacrylate, 1,6-hexanediol diacrylate, tetraethylene glycol diacrylate, trimethylolpropane triacrylate, tripropylene glycol diacrylate, pentaerythrityl triacrylate, pentaerythrityl tetraacrylate, ethylene glycol dimethacrylate, diethylene glycol dimethacrylate, triethylene glycol dimethacrylate, tetraethylene glycol dimethacrylate, polyethylene glycol 400 dimethacrylate, 1,3-butanediol dimethacrylate, 1,4-butanediol dimethacrylate, 1,6-hexanediol dimethacrylate, 1,12-dodecanediol dimethacrylate, neopentylglycol dimethacrylate or trimethylolpropane trimethacrylate.

Other suitable monomers C) are alkyl methacrylate or bisphenol A dimethacrylate, as well as vinyl ethers of polyhydric alcohols, such as butanediol divinyl ether. Polyfunctional acrylamides or methacrylamides, such as N,N'-methylenebisacrylamide, N,N'-methylenebismethacrylamide, N,N'-oxibismethylenebisacrylamide, N,N'-benzylidenebisacrylamide, terephthalidenetetraacrylamide, N,N'-butylidenebisacrylamide or methyl bisacrylamidoacetate. Divinylethylene urea is also suitable as monomer C).

Preferred monomers C) are 1,4-butanediol diacrylate, 1,6-hexanediol diacrylate, tetraethylene glycol diacrylate, ethylene glycol dimethacrylate, butanediol divinyl ether, N,N'-methylenebisacrylamide and divinylethylene urea.

The monomers C) are used in amounts of from 0.01 to 2, preferably from 0.02 to 0.5, % by weight, based on the total monomer mixture.

The amount of monomers C) is preferably such that the molar amount (N), based on the number of moles (P) of a copolymer which would be formed without the use of the monomer C), of monomers C) is characterized by the relationship $$P/N = a$$

where a is a decimal number from 1 to 5, preferably from 1.5 to 3. The variable (P) can be readily determined by a person skilled in the art from the ratio of the sum of the weights of monomers A) and B) to the average molecular weight $M_n$ of a polymer as obtained from these amounts of A) and B).

The novel copolymers are completely soluble in cosmetic alcohols, such as ethanol or isopropanol, and are gel-free.

The K values are from 30 to 50, preferably from 35 to 45. The K values are determined according to H. Fikentscher, Cellulose-Chemie, 13 (1932), 58–64 and 71–74, measured in 1% strength by weight alcoholic solution.

The novel copolymers are prepared by the method of free radical solution polymerization in alcohols, if necessary in a mixture of alcohols and water. Suitable alcohols are $C_1$–$C_4$-alkanols, the alcohols ethanol and isopropanol usually used in cosmetics being preferred.

The polymerization is carried out in the presence of suitable amounts of a compound which forms free radicals, such as organic azo or peroxo compounds, as polymerization initiators.

Examples of suitable initiators are diacyl peroxides, such as dilauroyl, didecanoyl and dioctanoyl peroxide, and peresters, such as tert-butyl peroxipivalate, tert-amyl peroxipivalate or tert-butyl peroxineodecanoate, and azo compounds, such as dimethyl 2,2-azobisisobutyrate, 2,2-azobisisobutyronitrile, 2,2-azobis(2-methylbutyronitrile) or 2,2-azobis(2,2-dimethylvaleronitrile).

The copolymers can be prepared by the batch process but are preferably prepared by the feed process, some of the solution of the monomer mixture being initially taken and the remaining part being fed in over a period of several hours. The monomers C) are preferably added only via the feed.

The duration of the monomer feed is usually such that the heat of polymerization evolved can be readily removed under the usual technical conditions.

The polymerization is advantageously carried out at from 60° to 100° C., preferably from 70° to 85° C., and the reaction can be carried out under autogenous pressure, atmospheric pressure or inert gas superatmospheric pressure. An example of a suitable inert gas is nitrogen.

It may also be advisable to carry out a postpolymerization in the presence of further free radical initiators after the polymerization. Particularly suitable free radical initiators for the post-polymerization are compounds of the general formula I $$R^1\text{—O—O—}R^2 \qquad \text{I}$$
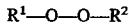

where $R^1$ is alkyl of 4 to 8 carbon atoms and $R^2$ is hydrogen or $R^1$ or is —$R^3$—O—O—$R^1$, where $R^3$ is linear or branched $C_4$–$C_{10}$-alkylene. Examples of suitable alkyl radicals are tert-butyl and tert-amyl. If $R^2$ is hydrogen, the compounds are alkyl hydroperoxides. A suitable free radical initiator is, for example, 2,5-dimethyl-2,5-bis(tert-butylperoxy)hexane. Preferred free radical initiators for the postpolymerization are di-tert-butyl peroxide and di-tert-amyl peroxide. The postpolymerization is advantageously carried out at from 110° to 150° C. until residual monomer contents of less than 50 ppm have been reached.

The novel copolymers have Fikentscher K values of from 30 to 50, preferably from 35 to 45. They are soluble in alcohols usually used for cosmetics, such as ethanol or isopropanol, or mixtures thereof with water, to give a clear solution and are gel-free. It is particularly advantageous that relatively high K values can also be obtained in a controlled manner and the resulting copolymers have good film formation properties.

The novel copolymers are suitable for use as film formers in hair cosmetic formulations, such as hairsprays, hair setting compositions and styling creams.

EXAMPLES

The turbidity of the aqueous copolymer solutions was determined by nephelometric turbidity measurement (modified method according to DIN 38 404). In this method of measurement, the scattering of light after passage through the measuring solution is determined photometrically, this scattering being governed by the interaction between the light rays and the particles or droplets in the solution, the number and size of which account for the degree of turbidity. The variable measured is expressed in nephelometric turbidity units (NTU) and is measured at 25° C. and in 10% strength by weight aqueous solution and specified by calibration on the basis of formazin as an artificial turbidity agent. The higher the NTU value, the more turbid is the solution.

The residual contents of N-vinylpyrrolidone and vinyl acetate in the solutions were determined by gas chromatographic analysis (limit of detection 50 ppm) or liquid chromatographic analysis (limit of detection 1 ppm).

The polymers prepared in Examples 1 to 3 are completely gel-free, ie. no gel particles were detectable when the polymer solution was spread to give a film.

The K values were measured in 1.0% strength by weight ethanolic solution at 25° C.

The polymerization was carried out using a 5 l stirred laboratory kettle which was very substantially freed from traces of oxygen by flushing with nitrogen.

EXAMPLE 1

Copolymer of 30% by Weight of N-Vinylpyrrolidone and 70% by Weight of Vinyl Acetate in Ethanolic Solution The following solutions were first prepared:
1. Solution 1, consisting of 450 g of N-vinylpyrrolidone, 1050 g of vinyl acetate and 870 g of ethanol.
2. Initiator feed, consisting of 3 g of tert-butyl peroxypivalate dissolved in 100 g of ethanol.
3. Initially taken mixture, consisting of 200 g of solution 1 and 10 g of initiator feed.
4. Monomer feed, consisting of 2120 g of solution 1 and 4 g of divinylethylene urea.

The initially taken mixture was introduced into the stirred laboratory kettle and heated to an internal temperature of 70° C. at a nitrogen pressure of 1.5 bar. After initiation of the polymerization, detectable from the increase in viscosity and the exothermic reaction, the monomer feed and the initiator feed were started simultaneously. The initiator feed was introduced at a constant rate in the course of 8 hours, and the monomer feed in the course of 7 hours. In order to eliminate residual monomers, the internal temperature of 70° C. was maintained for a further hour, after which a solution of 9 g of 2,5-dimethyl-2,5-di(tertbutylperoxy)hexane in 580 g of ethanol was metered in and the closed kettle was heated at 130° C. for 8 hours.

The resulting clear, colorless and viscous solution had a solids content of 50.0%, the K value of the product (measured in 1% strength solution in ethanol) was 43.4 and a solution having an NTU value of 2.8 was obtained on dilution of the solution to a solids content of 5% with ethanol. The residual monomer values were less than 50 ppm, both for N-vinylpyrrolidone and for vinyl acetate.

COMPARATIVE EXAMPLE 1

Copolymer of 30% by Weight of N-Vinylpyrrolidone and 70% by Weight of Vinyl Acetate in Ethanolic Solution, Having a Normal K Value The following solutions were first prepared:
1. Monomer feed, consisting of 450 g of N-vinylpyrrolidone, 1050 g of vinyl acetate and 870 g of ethanol.
2. Initiator feed, consisting of 3 g of tert-butyl peroxypivalate dissolved in 100 g of ethanol.

200 g of monomer feed and 10 g of initiator feed were initially taken in the stirred laboratory kettle, a nitrogen pressure of 1.5 bar was established and the mixture was heated to an internal temperature of 70° C. The further procedure was similar to Example 1.

The resulting clear, colorless and viscous solution had a solids content of 51.5%, the K value of the product (measured in 1% strength solution in ethanol) was 28.7 and a solution having an NTU value of 1.5 was obtained on dilution of the solution to a solids content of 5% with ethanol. The residual monomer values were less than 50 ppm, both for N-vinylpyrrolidone and for vinyl acetate.

EXAMPLE 2

Copolymer of 60% by Weight of N-Vinylpyrrolidone and 40% by Weight of Vinyl Acetate in Isopropanolic Solution, Having a High K Value The following solutions were first prepared:
1. Solution 1, consisting of 750 g of N-vinylpyrrolidone, 600 g of vinyl acetate and 800 g of isopropanol.
2. Initiator feed, consisting of 4 g of tert-butyl peroxypivalate dissolved in 100 g of ethanol.
3. Initially taken mixture, consisting of 200 g of solution 1 and 10 g of initiator feed.
4. Monomer feed, consisting of 1950 g of solution 1 and 3 g of divinylethylene urea.

The initially taken mixture was introduced into the stirred laboratory kettle, a nitrogen pressure of 1.5 bar was established and the mixture was heated to an internal temperature of 70° C. After initiation of the polymerization, detectable from an increase in viscosity and the exothermic reaction, the monomer feed and the initiator feed were started simultaneously. The initiator feed was introduced at a constant rate in the course of 8 hours, and the monomer feed in the course of 6 hours. Immediately after the monomer feed, a further 150 g of N-vinylpyrrolidone were metered in over two hours.

After the end of the initiator feed, 250 ml of isopropanol were distilled off. In order to eliminate residual monomers, a solution of 8 g of tert-butyl peroxypivalate in 150 g of isopropanol was metered in at an internal temperature of 70° C. in the course of 8 hours, and the temperature of 70° C. was maintained for a further 4 hours. After the addition of 750 g of water, the isopropanol was expelled by steam distillation and the solution brought to a solids content of 20% with water was spray-dried.

A light, white powder was obtained. The K value of the product (measured in 1% strength solution in ethanol) was 37.8 (39.3 in a second experiment). In aqueous solution (5% solids content), an NTU value of 2.1 was measured. The residual monomer values were 150 ppm for N-vinylpyrrolidone and less than 50 ppm for vinyl acetate.

COMPARATIVE EXAMPLE 2

Copolymer of 60% by Weight of N-Vinylpyrrolidone and 40% by Weight of Vinyl Acetate in Isopropanolic Solution, Having a Normal K Value The following solutions were first prepared:
1. Monomer feed, consisting of 750 g of N-vinylpyrrolidone, 600 g of vinyl acetate and 800 g of isopropanol.
2. Initiator feed, consisting of 4 g of tert-butyl peroxypivalate dissolved in 100 g of ethanol.

200 g of monomer feed and 10 g of initiator feed were initially taken in the stirred laboratory kettle, a nitrogen pressure of 1.5 bar was established and the mixture was heated to an internal temperature of 70° C. The further procedure was similar to Example 2.

A light, white powder was obtained. The K value of the product (measured in 1% strength solution in ethanol) was 31.7. In aqueous solution (5% solids content) an NTU value of 1.9 was measured. The residual monomer values were 150 ppm for N-vinylpyrrolidone and less than 50 ppm for vinyl acetate.

EXAMPLE 3

Copolymer of 50% by Weight of N-Vinylpyrrolidone and 50% by Weight of Tert-butyl Acrylate in Ethanolic Solution, Having a High K Value The following solutions were first prepared:
1. Monomer feed, consisting of 675 g of N-vinylpyrrolidone, 750 g of tert-butyl acrylate, 5 g of 1,4-butanediol dimethacrylate and 500 g of ethanol.
2. Initiator feed, consisting of 4 g of 2,2-azobis(2-methylbutyronitrile) dissolved in 150 g of ethanol.

The initially taken mixture, consisting of 75 g of N-vinylpyrrolidone, 75 g of ethanol and 15 g of initiator feed, was introduced into the stirred laboratory kettle, a nitrogen pressure of 1.5 bar was established and the mixture was heated to an internal temperature of 80° C. After initiation of the polymerization, detectable from an increase in viscosity and the exothermic reaction, the monomer feed and the initiator feed were started simultaneously. The initiator feed was introduced at a constant rate in the course of 8 hours, and the monomer feed in the course of 6 hours. In order to eliminate residual monomers, the internal temperature of 80° C. was maintained for a further hour, after which a solution of 9 g of di-tert-butyl peroxide in 825 g of ethanol was metered in and the closed kettle was heated at 140° C. for 8 hours.

The resulting clear, colorless and viscous solution had a solids content of 51.3%, the K value of the product (measured in 1% strength solution in ethanol) was 38.3 and a solution having an NTU value of 1.0 was obtained on dilution of the solution to a solids content of 5% with ethanol. The residual monomer values were less than 50 ppm, both for N-vinylpyrrolidone and for tertbutyl acrylate.

COMPARATIVE EXAMPLE 3

Copolymer of 50% by Weight of N-Vinylpyrrolidone and 50% by Weight of Tert-butyl Acrylate in Ethanolic Solution Having a Normal K Value The following solutions were first prepared:
1. Monomer feed, consisting of 675 g of N-vinylpyrrolidone, 750 g of tert-butyl acrylate and 500 g of ethanol.
2. Initiator feed, consisting of 4 g of 2,2-azobis(2-methylbutyronitrile) dissolved in 150 g of ethanol.

The initially taken mixture, consisting of 75 g of N-vinylpyrrolidone, 75 g of ethanol and 15 g of initiator feed, was introduced into the stirred laboratory kettle, a nitrogen pressure of 1.5 bar was established and the mixture was heated to an internal temperature of 80° C. The further procedure was similar to Example 3.

The resulting clear, colorless and viscous solution had a solids content of 50.6%, the K value of the product (measured in 1% strength solution in ethanol) was 30.7 and a solution having an NTU value of 0.9 was obtained on dilution of the solution to a solids content of 5% with ethanol. The residual monomer values were less than 50 ppm, both for N-vinylpyrrolidone and for tertbutyl acrylate.

We claim:

1. A copolymer which has a K value of from 30 to 50, obtained by free radical solution polymerization of
   A) from 15 to 84.99% by weight, based on the total amount of components A, B, and C, of at least one monomer selected from the group consisting of N-vinylpyrrolidone, N-vinylcaprolactam and N-vinylimidazole,
   B) from 15 to 84.99% by weight, based on the total amount of components A, B, and C, of at least one monomer selected from the group consisting of the vinyl esters of saturated $C_2$–$C_{24}$ monocarboxylic acids and the $C_1$–$C_{10}$ alkyl esters of acrylic or of methacrylic acid, and
   C) from 0.01 to 2% by weight, based on the total amount of components A, B, and C, of at least one monomer capable of free radical copolymerization and having at least two nonconjugated olefinic double bonds;
   in alcoholic solution.

2. A copolymer as defined in claim 1, containing N-vinylpyrrolidone or N-vinylcaprolactam as monomer A).

3. A process for the preparation of a copolymer, said copolymers being defined in claim 1, wherein a monomer mixture of
   A) from 15 to 84.99% by weight, based on the total amount of components A, B, and C, of one or more monomer selected from the group consisting of N-vinylpyrrolidone, N-vinylcaprolactam and N-vinylimidazole,
   B) from 15 to 84,99% by weight, based on the total amount of components A, B, and C, of at least one monomer selected from the group consisting of the vinyl esters of saturated $C_2$–$C_{24}$ monocarboxylic acids and the $C_1$–$C_{10}$ alkyl esters of acrylic or of methacrylic acid, and
   C) from 0.01 to 2% by weight, based on the total amount of components A, B, and C, of monomers capable of free radical polymerization and having at least two non-conjugated olefinic double bonds
   is polymerized by solution polymerization in alcoholic solution in the presence of a compound which forms free radicals.

4. A method of forming a film on an object, comprising applying to said object an effective amount of a copolymer as defined in claim 1.

5. A method of forming a film on an object, comprising applying to said object a hair cosmetic formulation containing an effective amount of a copolymer as defined in claim 1.

6. A hair cosmetic formulation containing a copolymer as defined in claim 1 as a film former.

* * * * *